United States Patent
Westcott

[11] Patent Number: 6,109,497
[45] Date of Patent: Aug. 29, 2000

[54] DISPOSAL RECEPTACLE FOR KNIFE BLADES

[76] Inventor: Richard S. Westcott, 817 NE. 117th St., Seattle, Wash. 98125

[21] Appl. No.: 09/227,071

[22] Filed: Jan. 5, 1999

[51] Int. Cl.[7] .................................................. A45C 1/04
[52] U.S. Cl. ...................... 224/679; 224/666; 224/901.8; 206/359
[58] Field of Search .................................... 224/679, 666, 224/901.8; 206/359, 370, 366

[56] References Cited

U.S. PATENT DOCUMENTS

| | | | |
|---|---|---|---|
| 4,114,780 | 9/1978 | Sharon | 206/359 |
| 4,730,376 | 3/1988 | Yamada | 206/359 |
| 4,903,390 | 2/1990 | Vidal et al. | 203/359 |
| 5,323,902 | 6/1994 | Palmer et al. | 206/366 |
| 5,381,922 | 1/1995 | Gladman et al. | 224/901.8 |
| 5,411,193 | 5/1995 | Culp | 206/366 |

*Primary Examiner*—Linda J. Sholl
*Attorney, Agent, or Firm*—Delbert J. Barnard

[57] ABSTRACT

A top wall (22), four side walls (26, 28, 30, 32) and a bottom wall (24) together enclose an inner space (46). The top wall (22) includes a narrow slot (34) sized to allow passage of a knife blade (44) through it, into the inner space (46). The walls (22, 24, 26, 28, 30, 32) form barriers to movement of knife blades (44) into and out from said inner space (46) other than through said slot (34). When the receptacle (10) is full of used knife blades (44), it is disposed of safely in any trash receptacle.

2 Claims, 3 Drawing Sheets

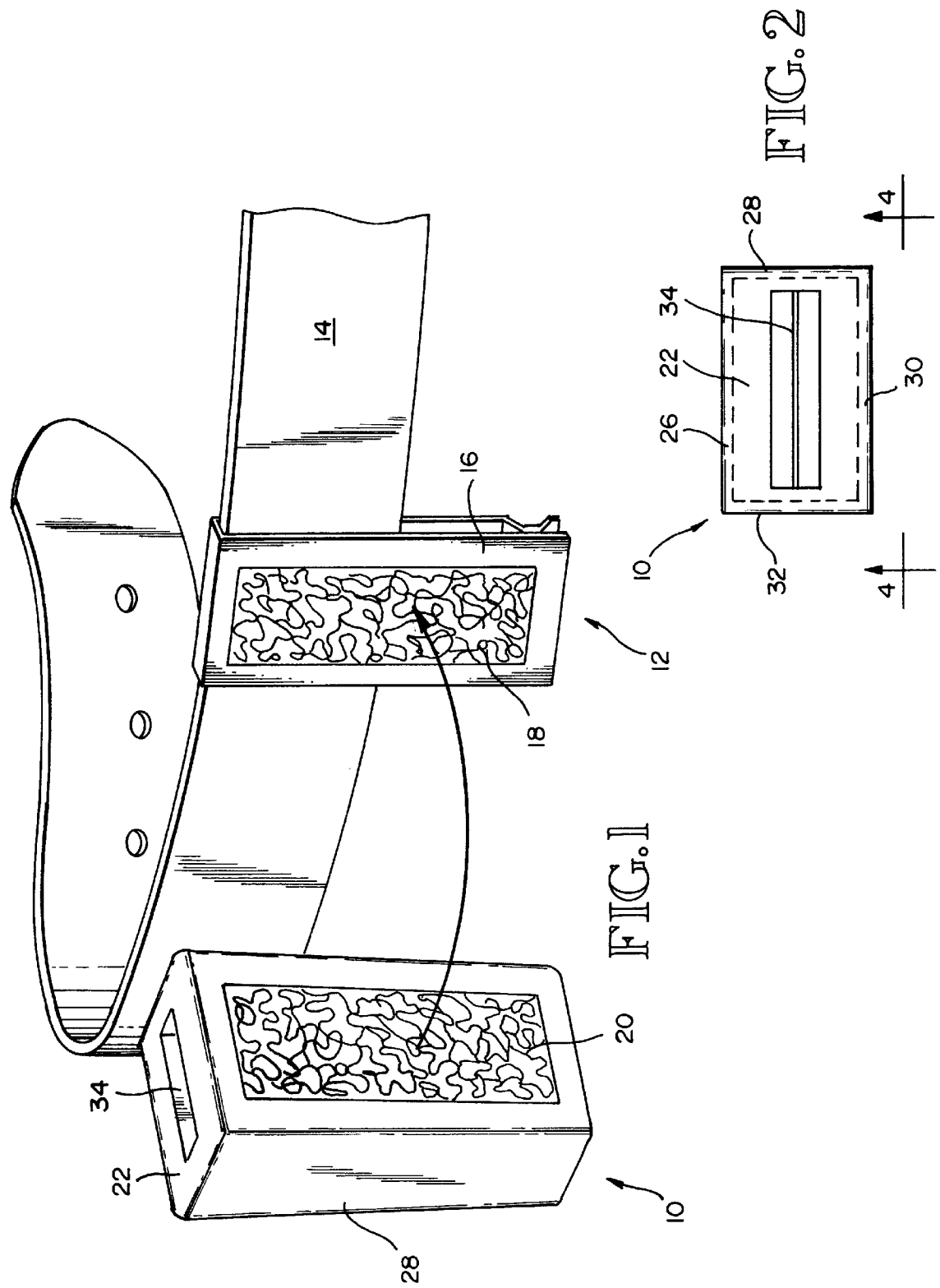

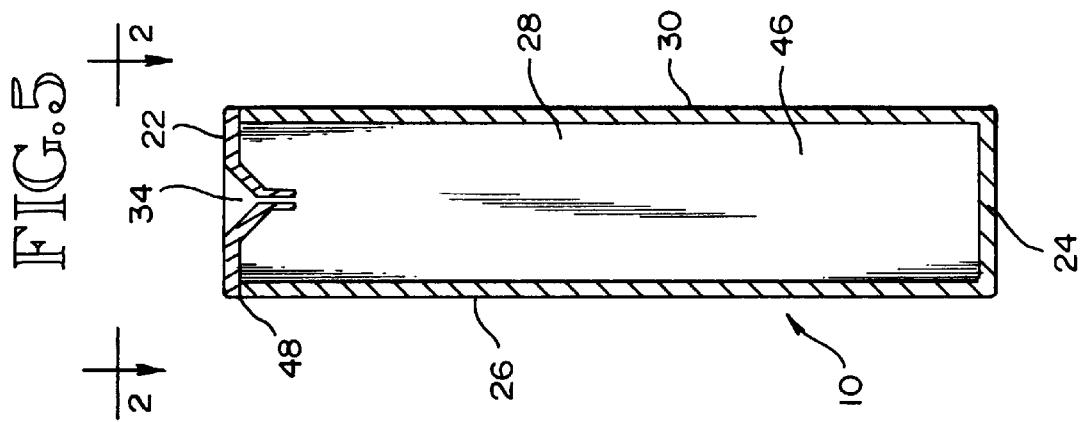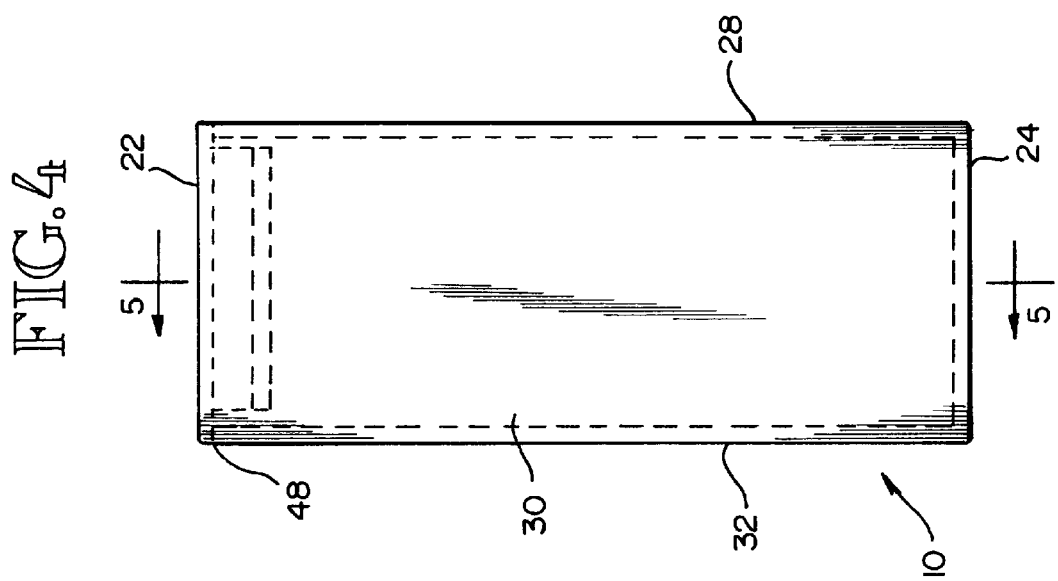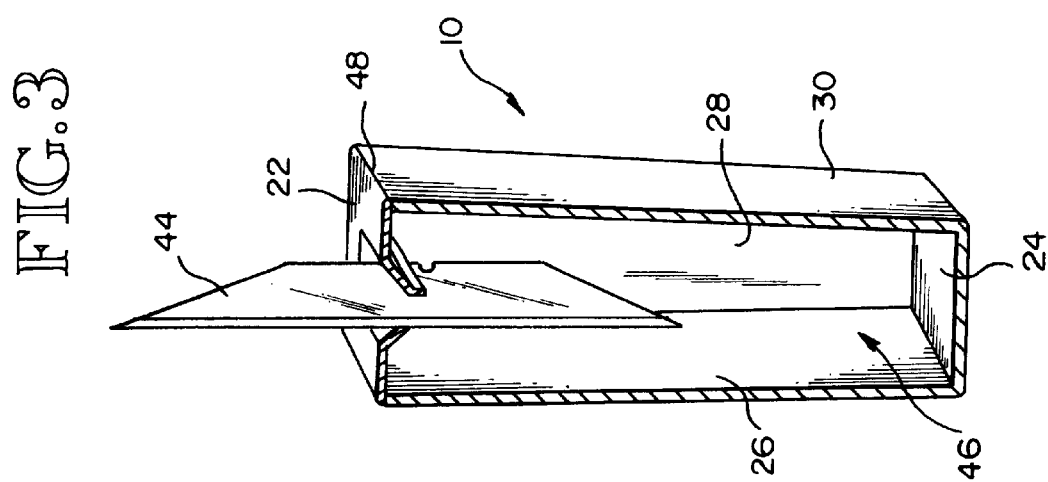

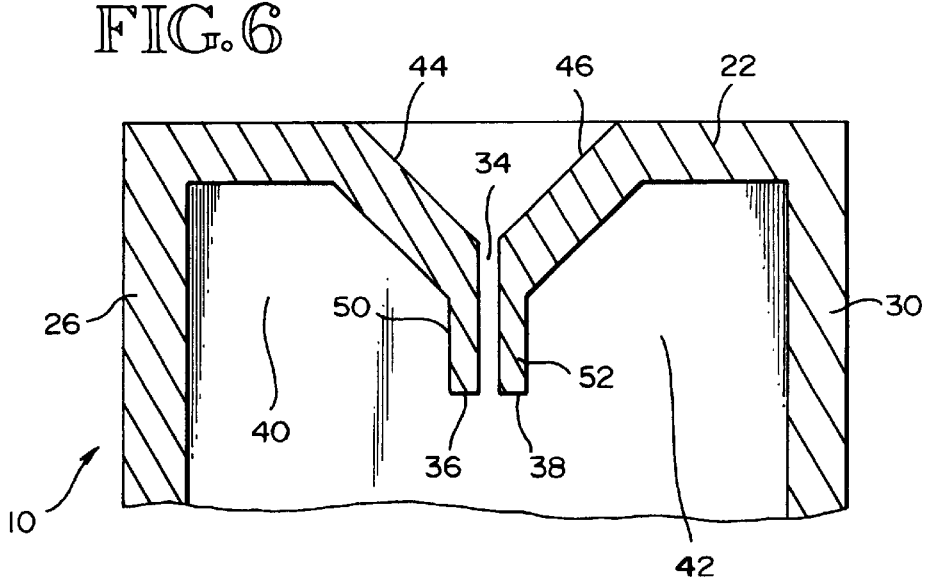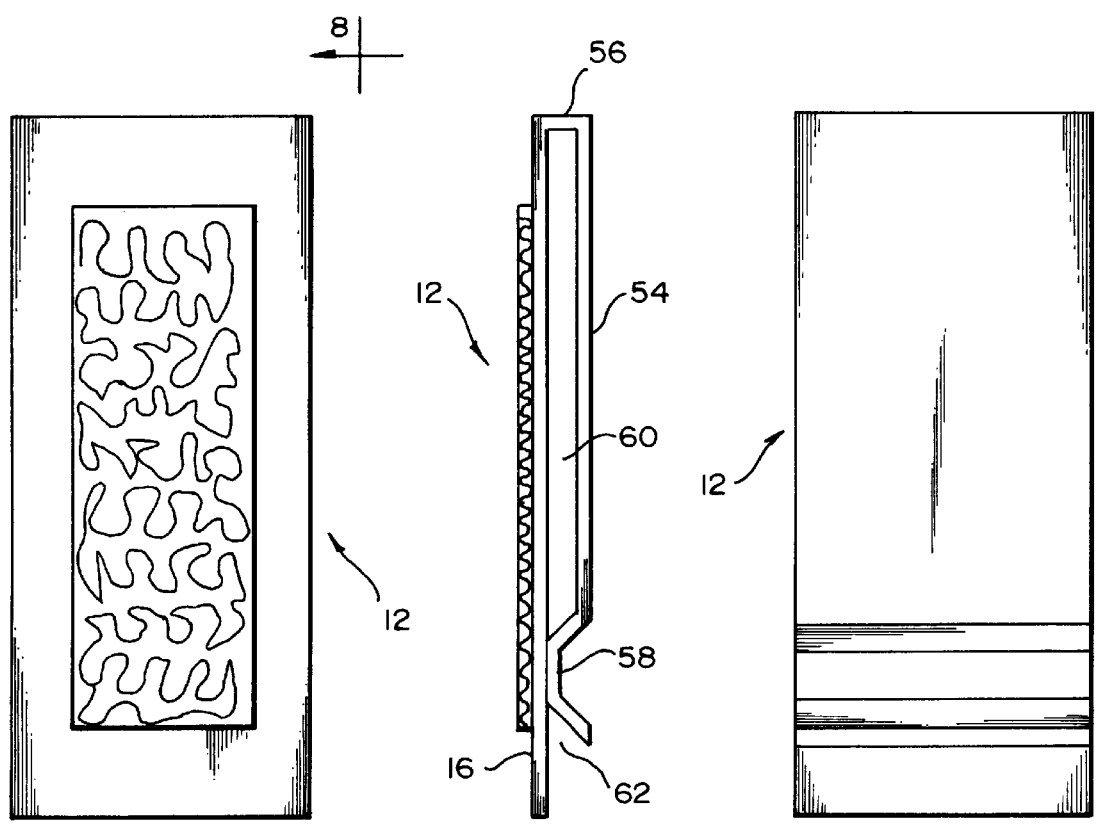

DISPOSAL RECEPTACLE FOR KNIFE BLADES

TECHNICAL FIELD

The present invention relates to the safe disposal of used blades from utility knives. More specifically, it relates to the provision of a small, inexpensive disposal receptacle in which used knife blades are deposited and when full of used knife blades is deposited in a trash receptacle.

BACKGROUND OF THE INVENTION

A "utility knife" is composed of a handle and a knife blade. The handle comes apart so that a blade can be inserted into or removed out from the handle. Utility knife blades have opposite ends that are pointed and are identical. This allows the blade to be turned end for end in the handle. The pointed end projects out from an end of the handle. After the pointed end has become dull, the blade is reversed end for end in the handle and the second end is used until it becomes dull. Then, the blade is removed and discarded and a new blade is inserted into the handle. Herein the term "utility knives" includes carpet knifes which are often termed "carpet knives". The term also includes any other knife with a disposable blade.

A problem in the construction industry is the safe disposal of used blades from utility knives. These blades are often left on the job site or are discarded loose in trash receptacles where they pose a safety hazard to anybody who comes in contact with them. There is a need of a personal blade disposal system which provides the individual with a safe, convenient and inexpensive way of disposing of used knife blades. It is a primary object of this invention to provide such a system.

DISCLOSURE OF THE INVENTION

According to the present invention, a disposal receptacle is provided for receiving used knife blades. The receptacle is basically characterized by a top wall, four side walls and a bottom wall, together enclosing an inner space. One of the walls, e.g. the top wall, includes a narrow slot sized to allow passage of a knife blade through it, into the inner space. The walls form barriers to movement of knife blades into and out from the inner space other than through the slot.

Inside the receptacle, the slot may be laterally outwardly bounded by narrow edges and the edges may be laterally outwardly bounded by spaces. The narrow edges and spaces prevent knife blades that are inside the receptacle from becoming realigned with the slot and inadvertently moving out from the receptacle through the slot.

On the outside of the receptacle, the slot-including wall may on opposite sides of the slot include converging surfaces leading into the slot for guiding a knife blade into the slot.

According to an aspect of the invention, the receptacle may be made in two parts. The first part may be the wall that includes the slot. The second part may be composed of the remaining five walls. The two parts are separately formed, such as by injection molding and then they are glued together to form the receptacle.

Another aspect of the invention involves providing a holder for the receptacle that is securable to a person. A pocket for the receptacle may be provided in a tool apron. A two component hook and loop fastener may be used, with one component being attached to a holder and the other component being attached to the receptacle. The holder may be a belt clip that is attachable to a workman's belt.

Preferably, the receptacle is made from an inexpensive plastic material. If desired, one or both parts of the receptacle may be made from a transparent or translucent material so that the user can see through it and see how many used blades are in the receptacle at any point of time.

According to an aspect of the invention, after the disposal receptacle is filled with used knife blades, the receptacle can be deposited safely in any trash receptacle. A new empty receptacle can be put into or attached to the holder as a replacement for the filled receptacle.

These and other advantages, objects, and features will become apparent from the following best mode description, the accompanying drawings, and the claims, which are all incorporated herein as part of the disclosure of the invention.

BRIEF DESCRIPTION OF THE DRAWINGS

In the drawings, like element designations refer to like parts throughout, and

FIG. 1 is a pictorial view of a knife blade receiving receptacle exemplifying the present invention, shown in a spaced relationship from a belt clip on a belt, such view showing components of a loop fastener on the receptacle and on the belt clip;

FIG. 2 is a top plan view of the blade receiving receptacle, such view being taken from the aspect identified by line 2—2 in FIG. 5;

FIG. 3 is a pictorial of the knife receiving receptacle of claim 1, with a foreground portion broken away for purposes of better illustrating a knife blade shown entering through a slot in the top of the receptacle into the interior of the receptacle;

FIG. 4 is a side elevational view of the knife blade receiving receptacle taken from the aspect of 4—4 of FIG. 2;

FIG. 5 is a longitudinal sectional view taken substantially along 5—5 of FIG. 4, such view showing the inside and outside regions bounding the knife blade slot in the top;

FIG. 6 is an enlarged scale fragmentary view of the upper portion of FIG. 5;

FIG. 7 is a side elevational view of the belt clip, looking towards the loop fastener component on the belt clip;

FIG. 8 is a side elevational view of the belt clip taken from the aspect of line 8—8 in FIG. 7; and FIG. 9 is a side elevational view of the belt clip looking towards the side opposite the side shown by FIG. 7.

BEST MODE FOR CARRYING OUT THE INVENTION

FIG. 1 shows a receptacle 10, embodying the present invention, positioned adjacent a belt clip 12. Belt clip 12 is shown positioned on a belt 14. Clip 12 has a front wall 16 that includes one component 18 of a hook and loop fastener used to attach the receptacle 10 to the belt clip 16. As will hereinafter be described in greater detail, the second component 20 of the hook and loop fastener is on the receptacle 10.

Referring to FIGS. 2–6, in preferred form, the receptacle 10 has a top wall 22, a bottom wall 24 and four side walls 26, 28, 30, 32. In accordance with the invention, one of the walls includes a blade receiving slot 34. In the illustrated embodiment, the slot-including wall is top wall 22. As best shown in FIGS. 5 and 6, inside the receptacle 10 the slot 34 is laterally outwardly bounded by narrow edges 36, 38. The edges 36, 38 are laterally outwardly bound by spaces 40, 42.

When a knife blade 43 (FIG. 3) is inserted through slot 34 into the interior 45 of the receptacle 10, the top end of the blade 43 will fall below the edges 36, 38. In order for a blade 43 to be removed from the receptacle 10, the upper end of the blade 43 would have to become realigned with the slot 34. The edges 36, 38 do not facilitate this alignment. They make alignment very difficult. Once the upper end of the blade is aligned with either space 40 or space 42, it will become less likely that the blade 43 will become aligned with the slot 34. As the result, the chances are very small that a blade 43 will move from the internal space 46 out through the slot 34.

As best shown by FIG. 6, the top wall 22 includes inwardly converging surfaces 44, 46 flanking the slot 34. Surfaces 44, 46 converge as they extend inwardly towards the slot 34. Whereas the configuration within the receptacle 10, in the region of the inner end of the slot 34, discourages knife blade movement through the slot 34, the surfaces 44, 46 encourage movement of a knife blade 44 to the slot 34.

The receptacle 10 may be made in two pieces by injection molding. The side walls 26, 28, 30, 32 and the bottom wall 24 may be formed as a single piece and the top wall 22 may be formed as a separate piece. FIG. 3 shows space 46 widening as it extends up from the bottom wall 24. This widening may occur both between walls 26, 30 and between walls 28, 32. This widening facilitates removal of the major piece 24, 26, 28, 30, 32 from its mold. After the two parts are made, the top wall 22 may be glued to the upper edges of the side walls 26, 28, 30, 32, at 48.

By way of typical and therefore non-limitive example, the receptacle 10 may measure about 2½–5 inches in length, between 1–2 inches in width and between ½ and 1½ inches in depth. In preferred form, the receptacle measures about three inches in length, about 1¼ inches in width and about ¾ inch in depth. The wall may be about 1/16 inch thick. The slot width may be about 25 mm.

Referring again to FIG. 6, the edges 36, 38 may be at the lower end of a pair of thin flaps 50, 52. The flaps 50, 52 are preferably resilient so that a knife blade 43 that is slightly wider than the slot 34 can be pushed through the slot 34 and into the inner space 45.

Referring to FIGS. 7–9, the clip 12 has a back part 54 that is connected to the front part 16 by an end part in the form of a bight 56. Back part 54 includes an indented region 56 which normally makes contact with the front part 16. The front and back parts 16, 54 and the bight 56 form what is in effect a spring. Clip 12 includes a belt opening 60 and a belt avenue 62 that is shaped to facilitate movement of the belt 14 between region 58 of back part 54 and front part 16. Once the belt is inside the space 60, as shown in FIG. 1, the spring energy in the clip 12 returns region 58 back into contact with part 16.

Elements 18, 20 are the two components of a hook and loop fastener. An example of this type of fastener is sold under the trademark VELCRO. When the belt 14 is on a user, and the clip 12 is on the belt 14, the user can move fastener component 20 on the receptacle 10 into engagement with fastener component 18 on clip 12. The engagement of the two fastener components 18, 20 will hold the receptacle 10 and its contents connected to the clip 12 until receptacle 10 is forcibly pulled away from clip 12 to break the hold that the fastener components 18, 20 have on each other.

If the slot 34 is put into one of the side walls 26, 28, 30, 32, it should be made long enough to permit a sideways insertion of the knife blade 44 through the slot 34. In place of the slot structure that is illustrated, the slot including wall may be a flat wall of uniform thickness in which a cut is made. The cut becomes the slot. The knife blade is then forced through the cut into the receptacle.

The illustrated and above described embodiments are only examples of the present invention and, therefore, are non-limitive. It is to be understood that many changes in the particular structure, materials and features of the invention may be made without departing from the spirit and scope of the invention. Therefore, it is my intention that my patent rights not be limited by the particular embodiments illustrated and described herein, but rather determined by the following claims, interpreted according to accepted doctrines of claim interpretation, including use of the doctrine of equivalents and reversal of parts.

What is claimed is:

1. A receptacle for used knife blades, comprising:
    a top wall, four sidewalls and a bottom wall together enclosing an inner space;
    said top wall including a narrow slot sized to allow passage of a knife blade through it, into the inner space;
    wherein on the outside of the receptacle the top wall includes converging guide surfaces leading into said slot, for guiding a knife blade into the slot;
    wherein on the inside of the receptacle, said slot is laterally outwardly bounded by slot sidewalls having narrow lower edges, and said slot sidewalls are laterally outwardly bounded by portions of said inner space; and
    said receptacle walls forming barriers to movement of knife blades into and out from said inner space other than through said slot.

2. The receptacle of claim 1, further comprising a belt clip that is connectable to a belt worn by a person, and a hook and loop fastener detachable connecting the receptacle to the belt clip, whereby a receptacle containing used knife blades can be pulled away from the belt clip and replaced by an empty receptacle.

\* \* \* \* \*